United States Patent [19]
Hammes

[11] Patent Number: 6,001,145
[45] Date of Patent: Dec. 14, 1999

[54] AIR PURIFICATION APPARATUS

[75] Inventor: Frank Hammes, Horn, Switzerland

[73] Assignee: Clinix GmbH, Switzerland

[21] Appl. No.: 08/961,737

[22] Filed: Oct. 31, 1997

[30] Foreign Application Priority Data

Nov. 1, 1996 [DE] Germany .............................. 196 45 096

[51] Int. Cl.⁶ .................................................. B01D 25/00
[52] U.S. Cl. ............................... 55/471; 55/480; 55/481; 55/493; 55/503; 55/472; 55/502
[58] Field of Search ............................... 55/472, 480, 481, 55/482, 493, 496, 503, 508, 511, 478, 486, DIG. 31, DIG. 18, 471, 473, 467, 502

[56] References Cited

U.S. PATENT DOCUMENTS

| | | | |
|---|---|---|---|
| 3,308,558 | 3/1967 | Orlando | 55/DIG. 31 |
| 3,966,442 | 6/1976 | Waters | 55/482 |
| 4,269,615 | 5/1981 | Zboralski et al. | 55/480 |
| 4,946,480 | 8/1990 | Hauville | 55/472 |
| 5,178,760 | 1/1993 | Solberg, Jr. | 55/503 |

*Primary Examiner*—Jay H. Woo
*Assistant Examiner*—Robert A. Hopkins
*Attorney, Agent, or Firm*—Lackenbach Siegel Marzullo Aronson & Greenspan, P.C.

[57] ABSTRACT

The invention relates to an air purification apparatus substantially comprising a suction part, a ventilator housing with one or several ventilators and one or more air filters disposed before or after the ventilator, wherein a housing implemented with a base comprises modular function parts disposed tower-like one above the other, one engaging the other in sealing fit and readily detachable one from the other and at least one pivoted lever disposed pivotably on the lateral portion of the housing by means of a pivot receptor in the direction of the arrow and extending over all parts of the housing from the outside and clamping them together. The air purification apparatus additionally fastenable on the ceiling is usable in particular as spot suction, as ventilation or overpressure or as clean-air purification apparatus.

31 Claims, 8 Drawing Sheets

AIR PURIFICATION APPARATUS

BACKGROUND OF THE INVENTION

1. Field of the Invention

The invention relates to an air purification apparatus. Such air purification apparatus have become known in a large variety of implementations. They substantially comprise a suction part, a ventilator housing, in which one or several ventilators are disposed, and one or several air filters disposed in front or after the ventilators in order to draw in the air from a specific suction opening, to force it through the ventilator housing and conduct it through the air filters in order to separate through the filters the dust or other floating particles.

2. Description of the Prior Art

The disadvantage of previously known air purification apparatus, which operate according to the dry-filter principle, is the inferior replaceability of the filters.

By that is understood the following:

In the previously known apparatus several different filter media are combined in a single filter element which entails the disadvantage that the filter element can only be exchanged as a whole which entails relatively high costs and, moreover, is often unnecessary because only one of the various filters types combined in the element, is contaminated and requires replacement while the others are not yet in need of replacement. This leads to the disadvantage that the individual filters of the air purification apparatus, as a rule, are not individually replaceable but rather can only be replaced as a whole filter element.

A further disadvantage of the known air purification apparatus is that the filters cannot be disposed in the housing of the air purification apparatus at different locations. For example, it may sometimes be desirable to place the rough-dust filter as closely as possible in the proximity of the suction opening of the apparatus in order to separate at this site the maximum quantity of rough dust and to protect other parts of the apparatus against this rough dust. In the known apparatus it is not possible to assign, for exam e to the rough-dust filter, more than one succeeding fine-dust filter because the sequence of filters and the number of filters in the known air purification apparatus is precisely predetermined and determined by the shape of the housing and the housing disposition.

A further disadvantage of the known air purification apparatus is thirdly that the filters as such cannot be exchanged rapidly, i.e. considerable disassembly work is required in order to remove such filters from the housing. It is herein known to close the housing with toggle lever closures or other clamping closures which can only be opened with great effort.

A further, fourth, disadvantage of the known air purification apparatus is that, as a rule, in the known apparatus the motor part is disposed last directly in front of the outflow part. This entails the disadvantage that during the operation the motor itself emits foreign particles, for example particles due to friction in the bearings, plastic particles front ventilator vines and others so that the motor itself, due to its own activity, introduces particles into the space to be purified which leads to the fact that a clean-room atmosphere is not attainable.

SUMMARY OF THE INVENTION

The invention is therefore based on the task of further developing an air purification apparatus of the above cited type such that individual filters in the air purification apparatus can be disposed in such a way that they can be quickly exchanged in a simple manner and that the sequence of the filters and the various other function parts of the air purification apparatus (such as for example suction part or outflow part) can be varied within relatively wide options.

It is an essential characteristic of the invention that now according to the invention the discrete functional parts of the air purification apparatus are designed in the manner of modules and that the modules stacked one on top of the other (stackable) have the form of a tower-like structure wherein this structure is clamped together by at least one pivoted lever disposed on the outside.

With the provided technical teaching of an invention the substantial advantage results due to the modular realization of the discrete functional parts of the air purification apparatus and their stackability now the exchangeability of one of the individual modules against another can readily take place. In the present invention the use of a single pivoted lever is claimed; however, preferred is the use of two pivoted levers, spaced apart and pivotable toward one another, which overlap the modular and tower-like structure of the individual functional parts from the outside and clamp them together.

Thus, the essential advantage is obtained that with the opening of the pivoted levers, at the same time with the modules disposed in sealing fit one on top of the other, the sealing fit is opened and the modules can be lifted one from the other.

Therewith it becomes possible for the first time that each module in the manner of a drawer can be pulled in the horizontal direction from the towerlike structure of the apparatus and the modules are thus realized so that they are quickly exchangeable.

Therewith it becomes possible for the first time that the fine-dust filter seated above the ventilator housing (which is also installed in a module) can also be pulled out in the manner of a drawer and thus be rapidly replaceable. In this way, other functional parts such as outflow part, can also be replaceably pulled out of the towerlike structure.

Thus the further advantage results that the length of the pivoted lever is also variable so that when using relatively long pivoted levers, it is now possible to place onto the overall structure, after removing the upper outflow part, a further modular filter housing in order to attain other filter properties of the air purification apparatus.

It is thus possible to vary in any desired way the structure height of the modular-type overall housing and for this purpose only it is enabled to use different pivoted levers with different lengths and to place them accordingly in their pivot bearings.

The air purification apparatus according to the invention can be simply and reliably mounted on ceilings and can be used as a spot-suction, ventilation or overpressure apparatus or as pure-air purification apparatus.

For the purpose of mounting the apparatus on the ceiling, the air purification apparatus is latched with its base into a ceiling mount plate with the simple filter change being also ensured with this manner of mounting the apparatus on the ceiling. The filter module disposed between apparatus base and suction tank part is retained even when the apparatus pivoted lever is fully opened. The filter modules disposed between the outflow part and the ventilator housing part are held in such a way that with ready opening of the pivot arms the filter modules retained by the extension can be readily removed from the air purification apparatus without encountering any problems.

For the application as a spot-suction apparatus the air purification apparatus is implemented on the apparatus base with a connecting part for a spot-suction tube via which air can be specifically suctioned off toward the apparatus. The spot-suction apparatus is applicable in a variety of ways, for example in the field of work safety when suctioning off welding smoke.

The above described spot-suction connection can also be used to supplement the filter function of the air purification apparatus with a ventilation function. For this purpose, a duct with outside air connection is connected with the suction connection of the apparatus. The high-oxygen air is thus suctioned from the outside and, after it has passed through all of the filter stages of the apparatus, output into the ambient space.

The modular construction of the air purification apparatus also makes possible that the normally used outflow part is replaced by a special outflow part which can direct the ejected air stream by means of filter, tube or duct onto a specific site. Thereby a specific air purification effect onto a desired site is possible.

In the preferred embodiment of the invention the pivoted levers are implemented such that they engage with the upper arms, directed approximately horizontally, into associated receptors of the upper module so that all modules can be clamped from the top against a lower base part standing on the floor. The pivoted levers are seated in corresponding pivot bearings of the base part and are pivotably mounted there.

In a further preferred embodiment of the inventive concept it is provided that the pivoted levers are, in turn, connected with inwardly directed lever arms which, in the manner of levers supported on one side, are disposed on the insides of the particular pivoted lever. Each lever arm engages with a corresponding extension, fixedly disposed at the free end, an associated groove which is included in the transition region between the one module and the superjacent module. The bottom surface of the groove is herein assigned to the lower module while the cover surface of the groove is assigned to the upper module.

Both surfaces are implemented as press-free surfaces and extend at an angle (obliquely to the horizontal sloped upwardly) into the particular module.

If the pivoted lever is pivoted outwardly, the extension disposed on the free end of the particular lever arm pushes itself off at the upper press-free surface of the groove which is assigned to the upper module. In this way a separation movement directed in the vertical direction occurs between the upper module and the associated subjacent lower module.

The two modules are thus lifted one from the other and removed from their corresponding sealing fit.

The above described process is to be understood such that the described lever arm with the extension disposed on the free end extends into its associated opposing grooves in the region of the motor part and the suction tank connected therewith. Both modules are preferably screwed together so that both modules are lifted together if the lever arms are pivoted outwardly. But thereby the motor part and the suction tank connected therewith is lifted from the lower modular filter and simultaneously the further filter disposed above the motor part is also lifted and consequently can readily be pulled from the raised motor part.

When the pivoted lever is pivoted into the closure position, a twofold clamping occurs because, on the one hand, the pivoted levers extend with their extensions, directed approximately horizontally, over onto the upper outflow part disposed in the tower, which is clamped therewith and through the corresponding weight loading and the clamping force all other subjacent modules in mutual sealing fit are also clamped together.

In addition, tension is achieved thereby that the extension disposed on the free end of the lever arms and extending into the obliquely directed groove of the motor part, presses this motor part also downwardly and leaves it to be engaged in press fit on the subjacent module.

This leads to an absolutely sealing fit connection and a vibration-free and clean sealing fit between the engaged module edges of the superjacent modules is achieved.

It is incidentally preferred herein if in the region of these scaling surfaces, in addition, an encircling sealing cord is installed.

This sealing cord prevents the transfer of vibrations from the one module onto the superjacent or subjacent other module.

According to a further substantial characteristic of the invention it is provided that all modules are double-walled, i.e. they have an inner wall and an outer wall. It is preferred if the interspace between the inner and the outer wall is filled with a sound-absorbing material such as for example a plastic foam, epoxy foam or others.

According to a further substantial embodiment of the invention it is provided that the individual filters are retained with readily detachable clamping holder in the associated modules and the filter holders are inserted with friction closure with associated clamping elements into interspaces between the outer wall and the inner wall and are disposed in the region of vertically directed longitudinal ducts so that they are displaceable and fixable in the particular inner wall of the particular module.

In order for the modules to be readily exchangeable, it is provided that on the inner face of the particular pivoted levers receiving spaces for the placement of electrical lines are provided so that these lines can be guided from the base part close to the bottom in the inner spaces of the pivoted arms upwardly to the individual modules with the lines in this case being introduced from the inside of the particular pivoted lever in the direction from the outside into the modular ventilator part. Therefore power lines laid out in the inner space and connections which could make difficult pulling apart and removing the individual modules are avoided.

It is incidentally preferred if the operating part is disposed preferably in the region of the horizontally directed extensions of the pivoted levers since therewith also the lines associated with the operating part can be guided along in the particular pivoted lever without the need to guide the lines for the operating part through the modular housing.

The subject matter of the invention of the present invention is not only evident based on the subject matter of the individual patent claims but also from the combination of the individual patent claims with one another.

All specifications and characteristics disclosed in the documents, including the abstract, disclose specifications and characteristics, in particular the spatial embodiment depicted in the drawings, are claimed as being essential for the invention to the extent they are, individually or in combination, novel relative to prior art.

BRIEF DESCRIPTION OF THE DRAWINGS

In the following the invention will be explained in further detail in conjunction with drawings representing several implementation paths. Based on the drawings and their description further characteristics and advantages of the invention essential to the invention are evident. In the drawing depict:

FIG. 1 schematically an air purification apparatus according to the invention in the assembled state, FIG. 2 the embodiment according to FIG. 1 in the opened state with section representation of pivoted levers bilaterally in the swung-out state, FIG. 3 the embodiment according to FIG. 2 with modules lifted one from the other, FIG. 4 the section over two filter elements disposed one above the other in the manner of modules, FIG. 5 top view onto FIG. 4 omitting the filter element, FIG. 6 schematic sectional representation of the air purification apparatus before/in ceiling disposition, FIG. 7 schematic sectional representation of a spot-suction apparatus with tube arrangement, FIG. 8 schematic sectional representation of a ventilation or overpressure apparatus, FIG. 9 schematic sectional representation of a clean-air air purification apparatus with special outflow part.

Figure 1:
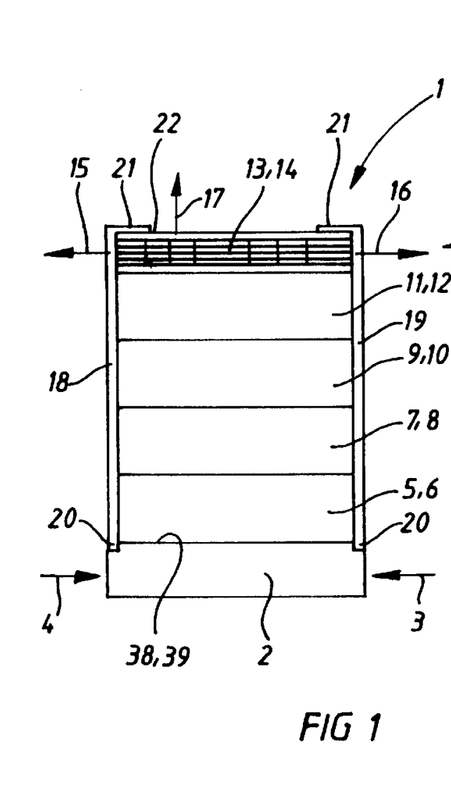

The air purification apparatus according to the invention comprises an overall housing 1 which comprises different modules disposed one above the other. In a base 2 are provided lateral (not further shown) suction openings through which the air is suctioned into the base 2 in the direction of arrows 3, 4. The air flows subsequently upwards into the direction of arrow 28. Directly onto the base is placed a first module 5 in sealing fit onto base 2 with this module 5 comprising a filter holder 6 and a filter 29 mounted therein so as to be readily exchangeable. Above this module 5 is disposed a further module 7 which is implemented as suction tank 8 and this suction tank 8 is connected with fastening means (not further depicted) with the superjacent module 9, which is implemented as ventilator housing 10 for receiving a ventilator.

Above the module 9 of the ventilator housing 10 is disposed a further module 11 which comprises a filter holder 12 in which is preferably disposed a fine-dust filter 29.

Above this module 11 is disposed in scaling fit an outflow part 13 comprising encircling outflow grids 14 through which the air flows out in the directions of arrows 15, 16 and potentially also upwardly in the direction or arrow 17. All of parts 2, 5, 7, 9, 11, 13 are thus assembled tower-like one above the other, one engaging the other in sealing fit and are implemented so as to be readily detachable one from the other with the exception that preferably the suction tank 8 is permanently connected with the ventilator housing 10.

Figure 6:
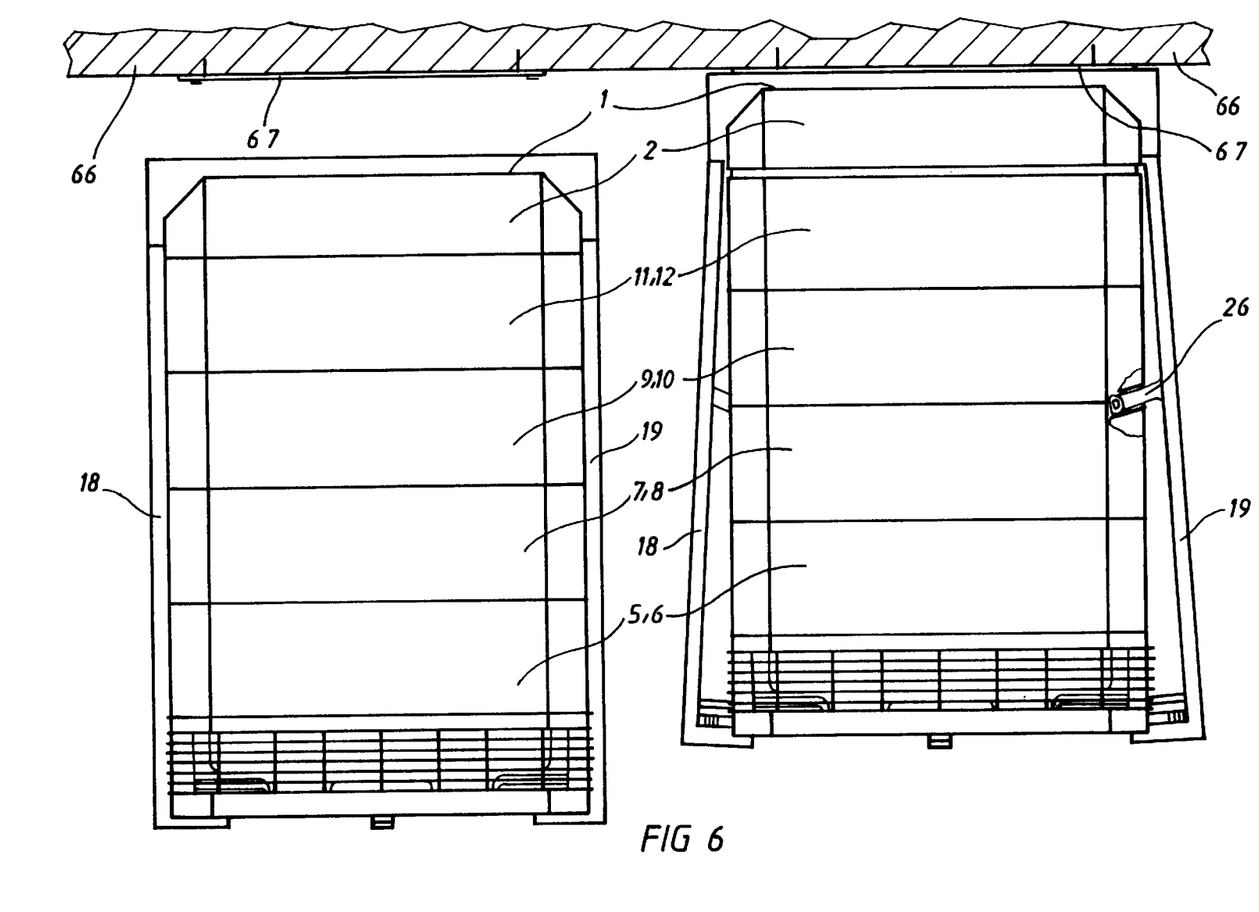

In order to subject the listed parts into abutment against one another, two pivoted levers 18, 19 disposed opposingly, are provided with each pivoted lever 18, 19, comprising a lower pivot receptor 20 depicted in further detail in FIG. 6.

Figure 2:
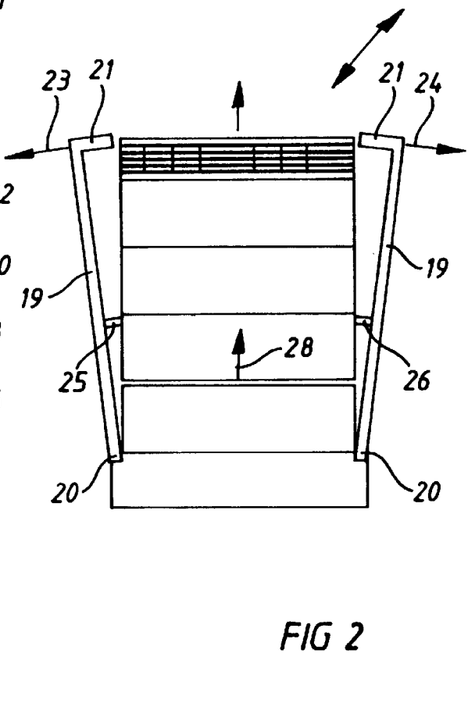

Each pivoted lever 18, 19 comprises an extension 21 directed approximately horizontally and inwardly, on whose upper side is preferably disposed the operating part of the entire air apparatus. If the pivoted lever 18, 19 is pulled apart in the directions of arrow 23, 24, the particular extension 21 disengages from a recess 22 (not further depicted) in the region of the air outflow part 13 and thus all modules 5, 7, 9, 11 can be lifted upwardly in the direction of arrow 28.

In a special further development of the invention is additionally provided that through the pivoting of the pivoted levers 18, 19 in the directions of arrows 23, 24, in addition, a lifting-off motion of the individual modules one from the other takes place in the direction of arrow 28. With reference to FIG. 2 it is shown that on the particular inside of each pivoted lever 18, 19 an inwardly directed pivoted arm 25, 26 is disposed which at its free front end is connected with an extension 50. This extension 50 extends into a groove 49 disposed in the interspace between module 9 of the ventilator housing 10 and the subjacent module 7 of the suction tank 8.

The bottom surface of groove 49 is formed by a press-free surface 46 which is sloped upwardly and obliquely inwardly with this press-free surface 46 and the lower portion of the groove being associated with the suction tank 8 while the cover surface of the groove 49 is implemented as press-free surface 47 whose slope is adapted approximately parallel to the lower cover surface 46.

The upper press-free surface 47 is here associated with the upper module (ventilator housing 10) and is implemented in the region of a recess 48 in the upper module block 10.

If the pivoted lever 19 is pivoted in the direction of arrow 23 about is lower pivoted receptor 20, the extension 50 pushes itself off at the free front end of the pivoted arm 26 on the upper press-free surface 47, and therewith the entire module structure is lifted upwardly out of modules 7, 9 in the direction of arrow 28.

Figure 3:
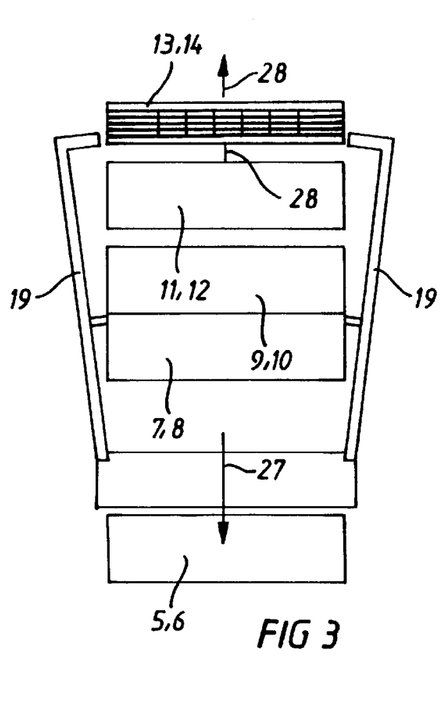

This leads to the lift-off movement shown in FIG. 3 between the module structure of modules 7, 9 and the subjacent module 5.

Module 5 can thus be readily pulled in the horizontal direction from the tower-like assembly in the direction of arrow 27 in the manner of a drawer.

FIG. 3 does indeed show the removal in the vertical direction; however, this has only been shown in this way for reasons of drawing. However, in reality the module 5 is pulled in the horizontal direction in direction of arrow 27 from the subjacent base 2 in the outward direction.

Thus, it can be readily detached from the assembly since the superjacent modules 7, 9 had been lifted upwardly in the direction of the lifting movement (direction of arrow 28).

Thus the ready exchangeability is given of the lower module 5 with the filter 29 preferably comprised therein and preferably implemented as rough-dust filter.

Figure 4:
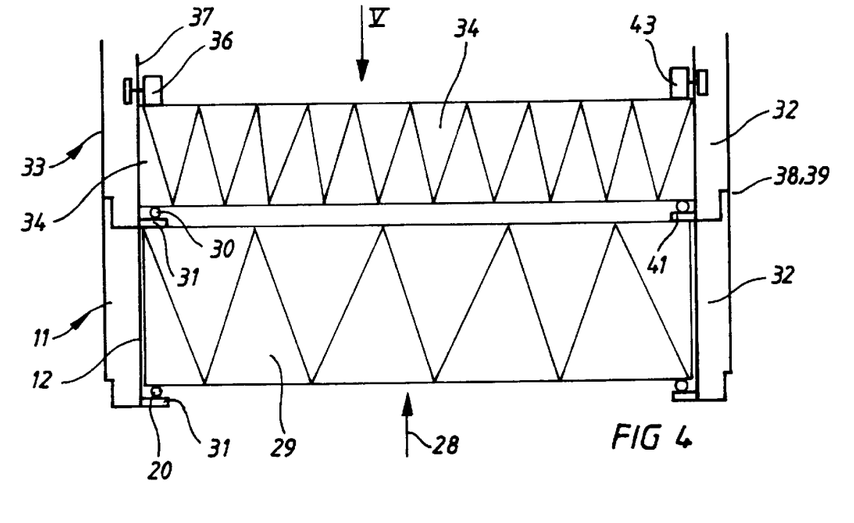

But now simultaneously also the upper module 11 can be removed from the module assembly, lifted up, of modules 7, 9 as is shown in FIG. 3 or in expansion of FIG. 3 onto the uppermost module 11 a further module 33 can be: placed which, as is also evident in FIG. 4, comprises a filter 34 (fine filter) which is held in a corresponding filter holder 36.

As an expansion of FIG. 3, FIG. 4 shows that onto the uppermost module 11 a further module 33 can be placed which also comprises a filter 34 held in a corresponding filter holder.

The pivoted levers 18, 19 would in this case be replaced for similar longer pivoted levers and onto the entire assembly, now of greater height, again the outflow part 13 would be placed so as to seal and could subsequently—precisely as described previously—be clamped together.

FIG. 4 shows the sealing fit of the individual modules, which also applies to and is valid for each shown in the previously depicted embodiment example FIG. 1 to FIG. 3.

It is evident that each module comprises an approximately tank-form structure and is implemented with double walls. Each comprises an outer wall and an encompassing inner wall which is implemented as a filter holder.

Figure 5:
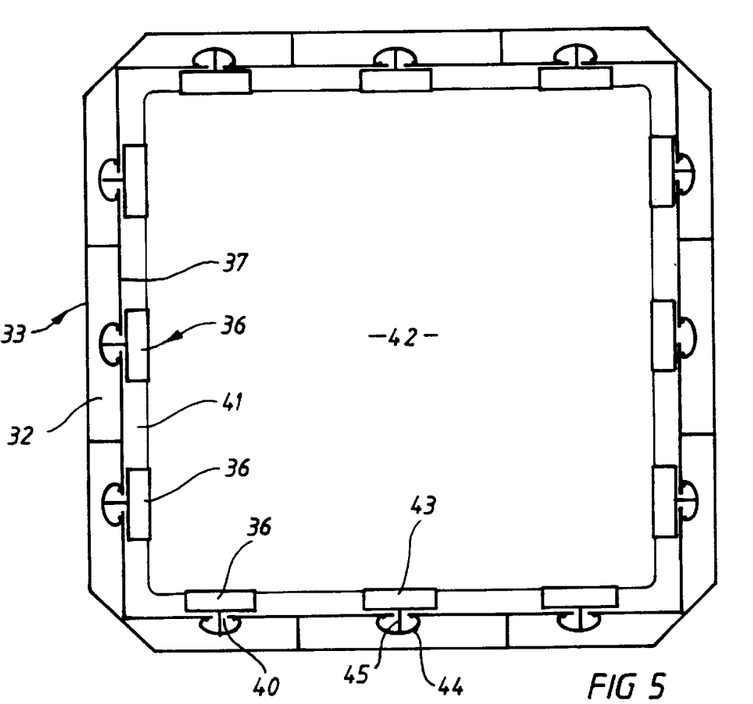

The details of this structure will be described in further detail in conjunction with FIG. 5 and with reference to the upper module 33.

Thus, an all encompassing self-contained outer wall is available which via an interspace 32 is spaced apart from an inner encompassing inner wall 37.

This inner interspace 32 is preferably foamed or filled with other noise-absorbing media.

In the inner wall 37 are now implemented longitudinal grooves 40 which are spaced apart one from the other and extend in parallel. Into these longitudinal grooves 40 is set under clamping a filter holder 36 which comprises substantially an inner clamping block 43 and a web 45 connected integrally with the material of the clamping block 43, which web extends through the particular longitudinal groove 40 and which is connected at its outer end with an approximately U-shaped clamping element 44 which is in contact with its free outer ends while exerting clamping force and under frictional closure on the outer surfaces of the inner wall 37.

Module 33 forms an inner central recess 42 which is bound toward the outside in the direction toward the inner wall 37 by an encompassing stop wall 41 inclined approximately horizontally. Onto this stop wall 41 is placed the filter 34, not further shown in FIG. 5, and where all clamping blocks 43 are removed from their longitudinal grooves 40. After placing the filter 34 into the recess 42, with the filter coming sealingly into contact with its outer edge on the stop wall 41, the clamping blocks 43 are set into the longitudinal grooves 40 and displaced downwardly so that the clamping blocks 43 then under the clamping effect, as shown in FIG. 4, come to rest on the upper encompassing edge of filter 34.

For a better sealing of the filter 34 it is additionally provided that between the underside of the filter and the associated stop wall 41 in each instance an encompassing sealing ring 30 is disposed.

In this way two filters 29, 34 are built one on top of the other like a tower and can be readily exchanged.

Each module tank comprises an offset extension 31 which forms an interspace 38 with an inserted round cord 39 with the outer wall of the subjacent module extending into this interspace 38 so as to form a seal as is shown in FIG. 4.

A further advantage of the air purification apparatus—namely the capability of an additional suspension on the ceiling—is not shown in FIG. 6. In this case the air purification apparatus is latched with the housing 1 with its base 2 on a mounting sheet 67 secured on the ceiling 66 so that the air purification apparatus is suspended upside down on the ceiling 66 securely and simply removably.

In thus ceiling mounting of the air purification apparatus the simple filter exchange from the filter module 5 is also ensured since this is retained even with the complete opening of the bilateral pivot levers 18, 19 in the direction of arrow 23, 24. Filter module 11 disposed between the outflow part 13 and the ventilator housing 10 is also retained if the bilateral pivoted levers 18, 19 are not completely opened in the direction of arrow 23, 24 through the extension 21 of the particular pivoted levers 18, 19 such that the filter 29 can be removed without any problems from the filter holder 12 of this module 11.

Figure 7:
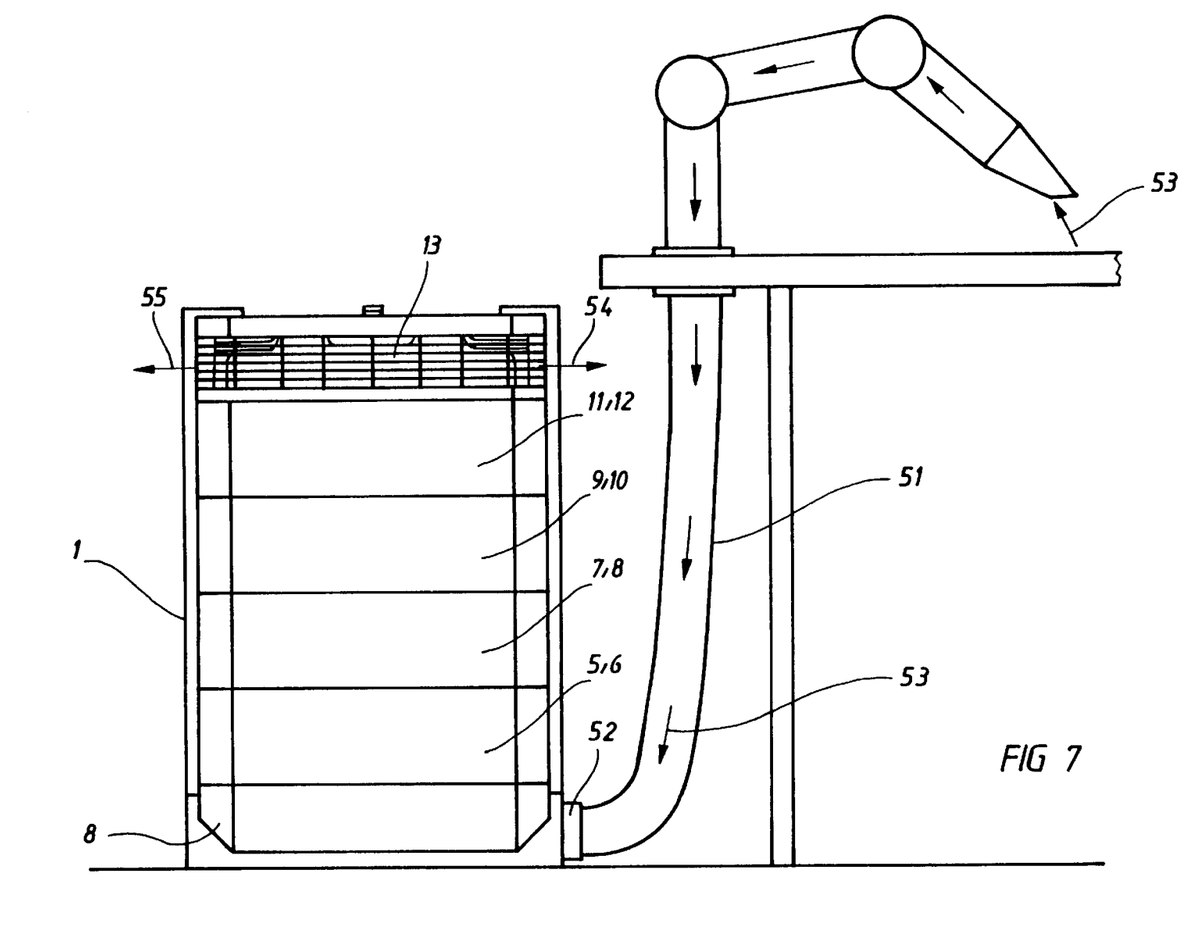

A special embodiment of the air purification apparatus as a spot-suction apparatus is evident in FIG. 7. To this end the air purification apparatus is provided with a spot-suction port 52 implemented on one side of the base 2 on the housing 1 for the connection of than suction tube 51. The air from the object to be suctioned off is conducted through the suction tube 51 into housing 1 of the air purification apparatus and flows there through the individual modules 5, 7, 9, 11 and leaves the housing 1 through the outflow part 13 in the direction of arrow 54, 55.

A spot-suction apparatus implemented in this way can be used in a large variety of ways, and is also suitable for example for enhancing work safety in the industry, in particular for welding smoke suction.

Figure 8:
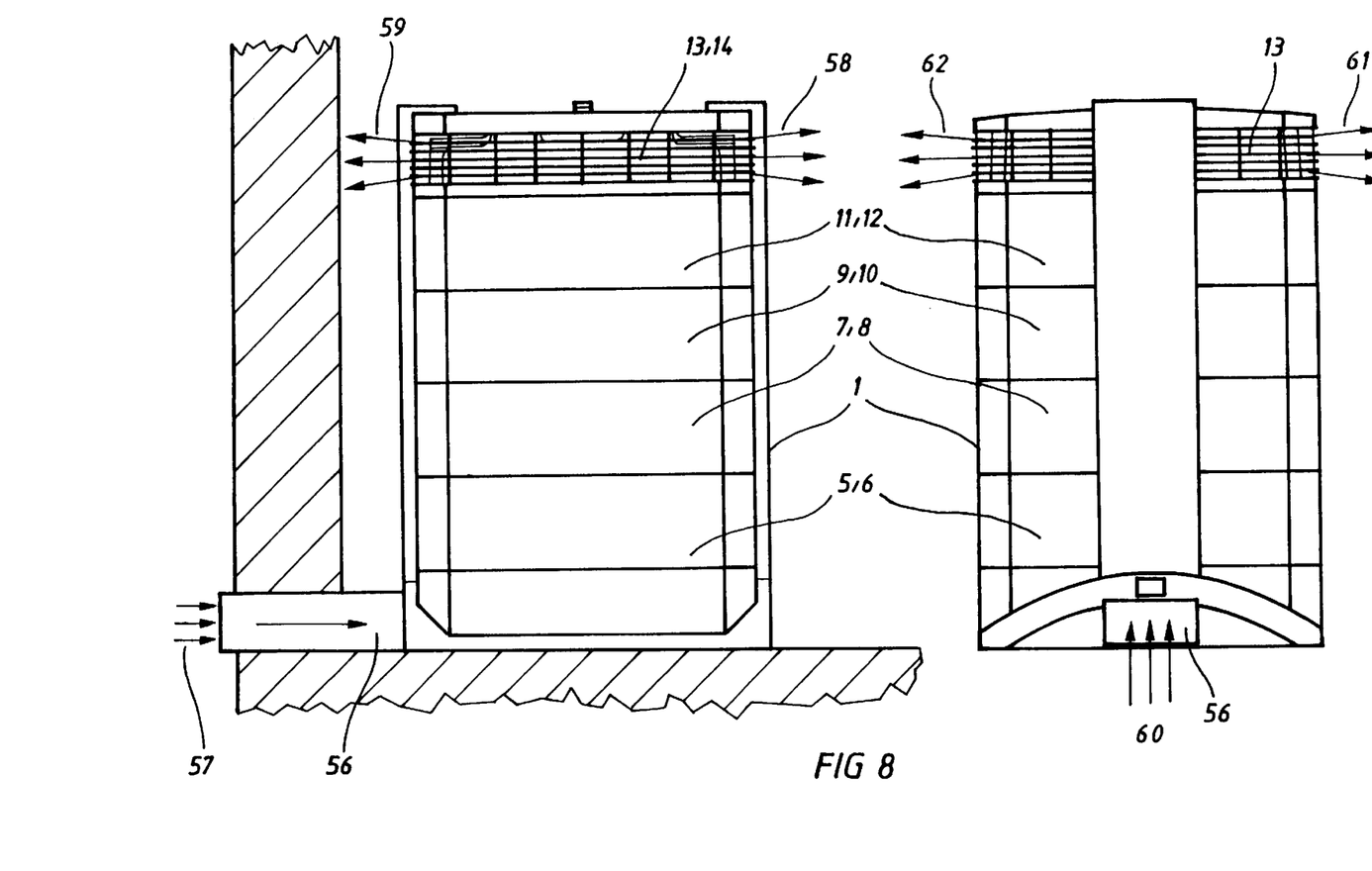

A further advantageous application option of the air purification apparatus according to the invention as ventilation or overpressure apparatus is shown in FIG. 8. For this purpose a duct 56, disposed on one side of housing 1 in the region of the base 2 or underneath the arcuately vaulted housing 1 and through which the surrounding air flows in the direction of arrows 57, 60, is connected with the suction port, not further depicted here, of the air purification apparatus so that the oxygen-rich air flowing into the apparatus in the direction of arrow 57, 60 through the duct 56 into housing 1 of the purification apparatus is purified through the filter modules 5, 11 and leaves the housing 1 after purification through the outflow part 13 in the direction of arrows 58, 59, 61, 62.

Figure 9:
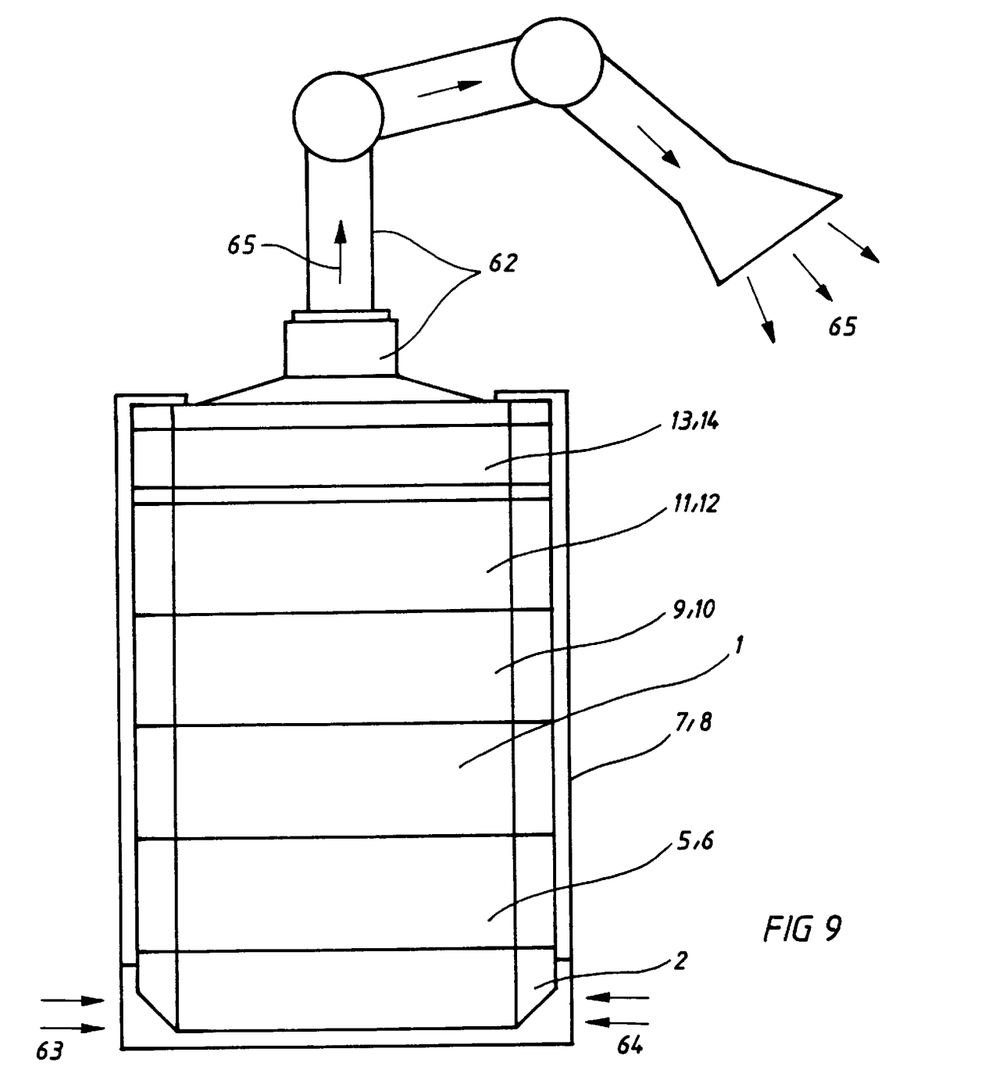

Lastly, the further advantageous application of the air purification apparatus as clean-air purification apparatus is depicted in FIG. 9.

For this purpose, the outflow part 13 of the housing 1 of the air purification apparatus is replaced by a special outflow part 62 which is implemented at the end with a funnel, tube or conduit. Therewith the air flowing in the direction of arrows 63, 64 into housing 1 of the air purification apparatus from below and flowing out through the filter modules 5, 11 purified and through the special outflow part 62 in the direction of arrow 65 can be specifically and intentionally directed onto the object to be purified.

The overall housing 1 is dimensioned relatively large which yields large ventilation cross sections. In a preferred embodiment, the housing 1 has outer dimensions of approximately 37×37 cm which results in a large ventilation cross section and correspondingly low ventilation noise.

The overall housing 1 is dimensioned relatively large which yields large ventilation cross sections. In a preferred embodiment, the housing 1 has outer dimensions of approximately 37×37 cm which results in a large ventilation cross section and correspondingly low ventilation noise.

Figure 10:
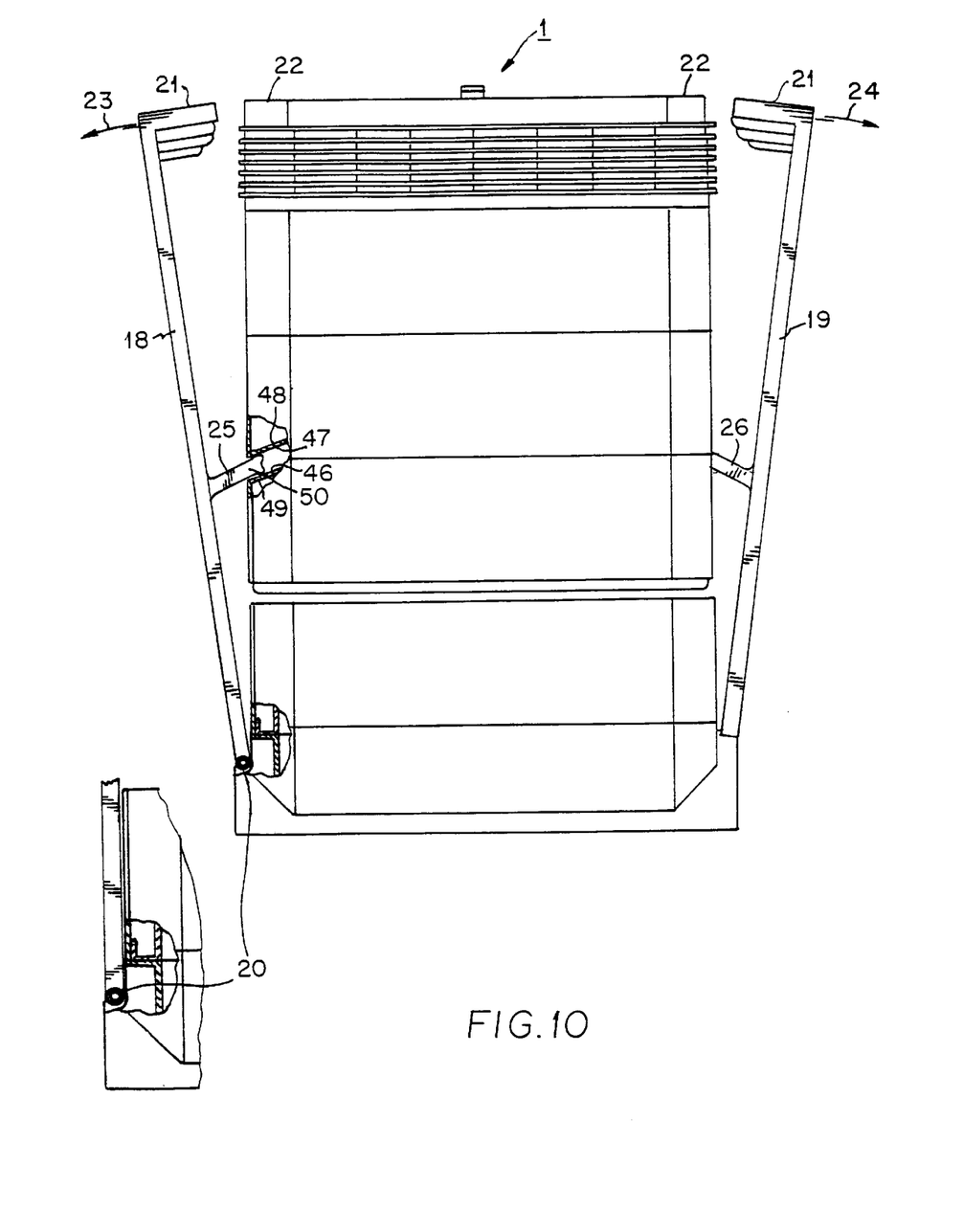
FIG. 10 is similar to FIG. 3 but showing some additional details for pivoting the levers and the extensions that will facilitate separation of the modules.
Figure 11:
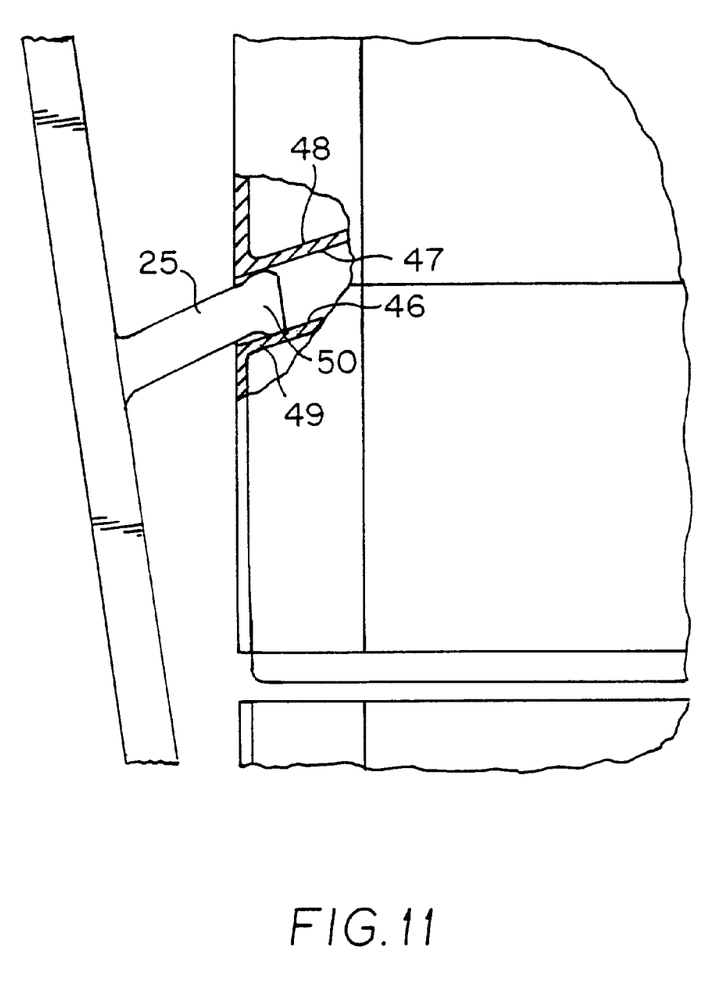
FIG. 11 is an enlarged view of the detail of FIG. 10, showing the cooperation of the extension 50 on the lever arm with the groove or recess in the housing of the air purification apparatus.

The pivoted levers (18, 19) have lever arms (25, 26), preferably two on each pivoted lever, preferably located on either side of the pivoted levers oriented parallel inwardly to the ventilator housing. At each end of the lever arms is situated a round extension (50).

Both the groove (49) and the lever arms (25, 26) are at a parallel upward angle when the purification apparatus is closed.

When the purification apparatus is opened by disengaging the extension (21) from the recess (22) and pivoting the two pivoted levers (18, 19) outward from the lateral portion of the housing, this causes the angle of the lever arms (25, 26) to increase upward and rise in the height of the extension (50) in relation to the other parts of the housing. This in turn lifts the module (7) and the module (9) which incorporate the suction tank (8) and the ventilator housing (10) in the direction of arrow (28). The module (7) and the module (9) are fixed together with screws for building a unit of two modules as seen from the outside. Outwardly they are of the same shape as the other modules but they are different from them inside and they can be separated easily by removing the screws.

Each pivoted lever engages with a corresponding extension into an associated groove which is located in the ventilation housing.

LEGEND

1 Overall housing
2 Base
3 Direction of arrow
4 Direction of arrow
5 Module
6 Filter holder
7 Module
8 Suction tank
9 Module
10 Ventilator housing
11 Module
12 Filter holder
13 Outflow part
14 Outflow grid
15 Direction of arrow
16 Direction of arrow
17 Direction of arrow
18 Pivoted lever
19 Pivoted lever
20 Pivot receptor
21 Extension
22 Recess
23 Direction of arrow
24 Direction of arrow
25 Lever arm
26 Lever arm
27 Direction of arrow
28 Direction of arrow
29 Filter
30 Sealing ring
31 Extension
32 interspace
33 Module
34 Filter (fine filter)
36 Filter holder
37 Inner wall
38 Interspace
39 Round cord
40 Longitudinal groove
41 Stop wall
42 Recess
43 Clamping block
44 Clamping element
45 Web
46 Press-free surface with push-off surface (bottom)
47 Press-free surface with push-off surface (top)
48 Recess (tipper module block)
49 groove (lower module block)
50 Extension
51 Suction tube
52 Spot-suction port
53 Direction of arrow
54 Direction of arrow
55 Direction of arrow
56 Duct
57 Direction of arrow
58 Direction of arrow
59 Direction of arrow
60 Direction of arrow
61 Direction of arrow
62 Outflow part
63 Direction of arrow
64 Direction of arrow
65 Direction of arrow
66 Ceiling
67 Mounting plate

I claim:

1. Air purification apparatus comprising a main housing defining a predetermined direction for an air flow through said housing and having a base and an outlet part spaced from each other along said predetermined direction; a plurality of cooperating in-line modules disposed one above the other between said base and said outlet part, said adjacent modules, base and outlet part forming in-line components adjacent ones of which normally engage each another in a sealing fit and are readily and selectively detachable one from the other, at least one of said modules comprising a ventilator unit, one of said modules comprising a filter holder including at least one air filter disposed on one side of said ventilator unit; at least one lever pivotally mounted on a lateral part of said main housing by pivot means, said at least one lever extending over and clamping all said in-line components together from the outside when said at least one lever is pivoted in a normally lateral inward position; and separating means attached to said at least one lever for selectively separating said ventilator unit in relation to a least one of said filter modules when said at least one pivoted lever is pivoted laterally outwardly from said main housing to facilitate selective removal of said at least one of said filter modules from said main housing.

2. Air purification apparatus as claimed in claim 1, wherein two pivot levers are arranged on opposite sides of said main housing to assume a corresponding distance one from the other and pivotable laterally inwardly by means of said pivot means on the lateral portion of the main housing toward each other and pivotable outwardly from the lateral portion of the main housing, extending from the outside over the tower-like structure of said in-line components of the housing and clamping these together.

3. Air purification apparatus as claimed in claim 1, wherein selected in-line components form a horizontally movable drawer structure and wherein said selected in-line components are rapidly exchangeable.

4. Air purification apparatus as claimed in claim 1, wherein all filters are disposed in selected modules in a particular filter holder such that they are rapidly exchangeable.

5. Air purification apparatus as claimed in claim 1, wherein said base comprises lateral suction openings, via which air is suctioned into the base, which subsequently flows through the filter modules and ventilator unit.

6. Air purification apparatus as claimed in claim 1, wherein one of said modules is placed adjacent to said base in sealing fit and comprises a filter holder with a readily exchangeable filter (29) comprising a rough-dust filter.

7. Air purification apparatus as claimed in claim 1, wherein said ventilator unit comprises a suction tank which is permanently fixedly fastened to a ventilator module.

8. Air purification apparatus as claimed in claim 1, wherein one of said modules downstream of said ventilator unit includes a fine-dust filter disposed in a filter holder.

9. Air purification apparatus as claimed in claim 8, wherein there is disposed in sealing fit downstream of said fine dust filter module an outflow grid of said outflow part, through which the air flows out in directions substantially normal to said in-line direction and also a direction substantially parallel to said in-line direction.

10. Air purification apparatus as claimed in claim 1, wherein there is joined to the module most remote from said base, a further module with a filter, said further module comprising an approximately tank-form structure provided with a self-contained outer wall, which, via an interspace (32) is spaced apart from an inner all-encompassing inner wall (37).

11. Air purification apparatus as claimed in claim 9, wherein each module tank forms an offset extension forming an interspace with an emplaced round cord and the outer wall of the subjacent module extends sealingly into this interspace.

12. Air purification apparatus as claimed in claim 1, wherein each pivoted lever comprises a lower pivot receptor and an extension, directed approximately horizontally inwardly, extends into a recess in the region of the outflow part and said extension, when pulling apart the pivoted levers in laterally outward directions disengages from the recess and thus enables the lifting-off of at least selected modules.

13. Air purification apparatus as claimed in claim 1, wherein the bottom surface of a groove is formed by a press-free surface which is inclined obliquely inwardly in the upward direction, and this press-free surface and the lower portion of the groove is assigned to the ventilator unit, while the cover surface of the groove is implemented as press-free surface whose slope is adapted approximately parallel to the lower press-free surface.

14. Air purification apparatus as claimed in claim 1, wherein for suspending the air purification apparatus on a mounting plate fastened on a ceiling, wherein the base of the air purification apparatus is provided with fastening means appropriate for this purpose and the air purification apparatus itself is disposed on the ceiling, even with the pivoted levers pivoted out in laterally outward directions to at least half of the pivot path through the extension of the particular pivoted lever, is secured against falling down.

15. Air purification apparatus as claimed in claim 1, wherein electric lines are guided in the pivoted levers in receiving spaces—implemented on the inner surface of the particular pivoted levers appropriate for this purpose, and wherein when the levers are pivoted in an outward direction, the motor automatically switches off.

16. Air purification apparatus as claimed in claim 1, wherein the pivoted levers are of variable lengths, whereby the structural height of the modular overall housing is variable in any desired way.

17. Air purification apparatus as claimed in claim 2, wherein the pivoted levers are of variable lengths, whereby the structural height of the modular overall housing is variable in any desired way.

18. Air purification apparatus as claimed in claim 10, wherein in the inner wall longitudinal grooves are implemented which extend in the vertical direction assuming a corresponding spacing with respect to one another and supporting said at least one filter holder under clamping force in each instance.

19. Air purification apparatus as claimed in claim 18, wherein each filter holder comprises substantially an inner clamping block and a web, whose material is formed integrally with the clamping block, extends through the particular longitudinal groove and is connected at its outer end with an approximately U-shaped clamping element, which, with its free outer ends, is in contact on the outer surfaces of the inner wall exerting a clamping force and under frictional closure.

20. Air purification apparatus as claimed in claim 19, wherein each filter module comprises an inner central recess which is bound toward the outside in the direction toward the inner wall by an encompassing stop wall inclined approximately horizontally, and onto this stop wall, after removing all clamping blocks from their longitudinal grooves, the filter can be placed and can be clamped again through the clamping blocks inserted again into their particular longitudinal grooves and displaced downwardly.

21. Air purification apparatus as claimed in claim 20, wherein, for better sealing of each filter between its underside and the associated stop wall, in each instance an encompassing sealing ring is disposed.

22. Air purification apparatus as claimed in claim 12, wherein for lifting the individual modules one from the other in an inline direction of said filter modules and ventilator unit, the pivoted levers pivoted outwardly from said lateral portion of said main housing on the particular inside of the particular pivoted lever have disposed a lever arm directed inwardly, which at its front free end is connected in each instance with an extension with the latter engaging a groove disposed in the interspace between the module of the ventilator housing and the subjacent module of the suction tank.

23. Air purification apparatus as claimed in claim 13, wherein the upper press-free surface is associated with the upper module of the ventilator housing and is implemented in the region of a recess in the upper module block.

24. Air purification apparatus as claimed in claim 1, wherein the air purification apparatus can be applied especially as spot-suction, as ventilation or overpressure or as clean-air purification apparatus.

25. Air purification apparatus as claimed in claim 1, wherein the air purification apparatus is applicable as a spot-suction apparatus and wherein the air purification apparatus is implemented with a spot-suction port disposed on one side of the base of the housing for connecting a suction tube.

26. Air purification apparatus as claimed in claim 24, wherein the air purification apparatus applicable as spot-suction apparatus is implemented with a spot-suction port disposed on one side of the base of the housing for connecting a suction tube.

27. Air purification apparatus as claimed in claim 1, wherein the air purification apparatus is applicable as a ventilation or overpressure apparatus and wherein the air purification apparatus is implemented with a duct, connected to the apparatus suction port, through which air flows through the filter modules and ventilator unit.

28. Air purification apparatus as claimed in claim 24, wherein the air purification apparatus applicable as ventilation or overpressure apparatus is implemented with a duct, connected to the apparatus suction port, through which air flows through the filter modules and ventilator unit.

29. Air purification apparatus as claimed in claim 1, wherein the air purification apparatus is applicable as a clean-air purification apparatus and wherein the air purification apparatus is implemented with an outflow part in the form of a funnel, tube or conduit or the like, through which air flows through the filter modules and ventilator unit and subsequently through the outlet of the funnel, tube, or conduit.

30. Air purification apparatus as claimed in claim 24, wherein the air purification apparatus applicable as clean-air purification apparatus is implemented with an outflow part in the form of a funnel, tube or conduit or the like, through which air flows through the filter modules and ventilator unit and subsequently through the outlet of the funnel, tube, or conduit.

31. A method of selectively removing filters from an air purification apparatus comprising the steps of providing a main housing defining a predetermined direction for an air flow through said housing and having a base and an outlet part spaced from each other along said predetermined direction; arranging a plurality of cooperating in-line modules disposed one above the other between said base and said outlet part, said adjacent modules, base and outlet part forming in-line components for normally providing a sealing fit and to be readily and selectively detachable one from the other, at least one of said modules comprising a ventilator unit, one of said modules comprising a filter holder including at least one air filter disposed on one side of said ventilator unit; mounting at least one lever pivotally on a lateral part of said main housing for extending over and clamping all said in-line components together from the outside when said at least one lever is pivoted in a normally lateral inward position; and selectively separating said ventilator unit in relation to at least one of said filter modules when said at least one pivoted lever is pivoted laterally outwardly from said main housing with a separating member on said at least one lever to facilitate selective removal of said at least one of said filter modules from said main housing.

\* \* \* \* \*